United States Patent
Ryu et al.

(10) Patent No.: US 6,838,416 B2
(45) Date of Patent: Jan. 4, 2005

(54) HERBICIDAL 5-BENZYLOXYMETHYL-1, 2-ISOXAZOLINE DERIVATIVES

(75) Inventors: Eung-Kul Ryu, Taejeon-si (KR); Hyoung-Rae Kim, Taejeon-si (KR); Dong-Ju Jeon, Taejeon-si (KR); Jong-Whan Song, Choongchungbuk-do (KR); Kyoung-Mahn Kim, Taejeon-si (KR); Jung-No Lee, Choongchungnam-do (KR); Hyoung-Cheul Kim, Sungnam-si (KR); Kyung-Sik Hong, Taejeon-si (KR)

(73) Assignee: Korea Research Institute of Chemical Technology (KR)

( * ) Notice: Subject to any disclaimer, the term of this patent is extended or adjusted under 35 U.S.C. 154(b) by 138 days.

(21) Appl. No.: 10/363,808

(22) PCT Filed: Sep. 5, 2001

(86) PCT No.: PCT/KR01/01500

§ 371 (c)(1),
(2), (4) Date: Mar. 6, 2003

(87) PCT Pub. No.: WO02/19825

PCT Pub. Date: Mar. 14, 2002

(65) Prior Publication Data

US 2004/0023808 A1 Feb. 5, 2004

(30) Foreign Application Priority Data

Sep. 7, 2000 (KR) .......................................... 200052917

(51) Int. Cl.$^7$ ........................ A01N 43/74; C07D 261/04
(52) U.S. Cl. ........................................ 504/271; 548/240
(58) Field of Search ........................... 504/271; 548/240

(56) References Cited

U.S. PATENT DOCUMENTS

| 4,983,210 A | 1/1991 | Rheinheimer et al. |
| 5,262,388 A | 11/1993 | Munro et al. |

*Primary Examiner*—Kamal Saeed
(74) *Attorney, Agent, or Firm*—Muserlian, Lucas and Mercanti, LLP

(57) ABSTRACT

The present invention provided with novel 5-benzyloxymethyl-1,2-isoxazoline derivatives of the formula (1), their preparation method and their use as herbicides. The 5-benzyloxymethyl-1,2-isoxazoline derivatives according to the present invention have sufficiently high herbicidal activity against the weeds in the paddy field rice even at low dose rates and excellent selectivity to transferred rice in particular. As thus, the compounds of the present invention are typically useful as herbicides for control of paddy weeds in rice.

13 Claims, No Drawings

HERBICIDAL 5-BENZYLOXYMETHYL-1,2-ISOXAZOLINE DERIVATIVES

This patent application claims a benefit of priority from Korean Patent Application No. 2000-52917 filed Sep. 7, 2000, through PCT Application Serial No. PCT/KR01/01500 filed Sep. 5, 2001, the contents of each of which is incorporated herein by reference.

TECHNICAL FIELD

The present invention relates to novel 5-benzyloxymethyl-1,2-isoxazoline derivatives of formula 1, their preparation method and their use as herbicides.

BACKGROUND OF THE INVENTION

Some compounds having a 5-benzyloxymethyl-1,2-isoxazoline moiety have been known to be useful for herbicides. For example, U.S. Pat. No. 4,983,210 discloses, as herbicides, 3-substituted-5-benzyloxymethyl-1,2-isoxazoline, wherein the substituents may be selected from the group consisting of thienyl, alkyl, haloalkyl, cycloalkyl, substituted or unsubstituted phenyl, tetrahydrofuranyl, tetrahydrothiophenyl, pyrolidinyl, furanyl, pyrolyl, pyridyl. Some compounds disclosed in U.S. Pat. No. 4,983,210 showed to have herbicial activity in rapeseed or sunflowers under the upland condition tests in greenhouse. U.S. Pat. No. 5,262,388 also discloses 5-benzyloxymethyl-1,2-isoxazoline derivatives substituted with nitrophenyl group at 3-position. Further, JP No. 09-143,171 discloses 5-benzyloxymethyl-1,2-isoxazoline derivatives substituted with carbonyl moiety at 3-position. 143,171 discloses 5-benzyloxymethyl-1,2-isoxazoline derivatives substituted with carbonyl moiety at 3-position. However, there has been a need for development of the novel agents with the highly herbicidal activity and selectivity in crops.

The present investigation has involved the synthesis of the compounds of the formula I, which have not been ever developed as herbicides and have the improved herbicidal activity and selectivity in crops, particularly in paddy rice.

SUMMARY OF THE INVENTION

The objective of the present investigation is to provide novel 5-benzyloxymethyl-1,2-isoxazoline derivatives of the formula I.

Another objective of the present investigation is to provide a preparation method of the said 5-benzyloxymethyl-1,2-isoxazoline derivatives.

The further objective of the present investigation is to provide herbicidal compositions comprising the said 5-benzyloxymethyl-1,2-isoxazoline derivatives as an active ingredient.

The herbicidal compositions according to the present investigation have high herbicidal activity against paddy weeds and high selectivity in rice.

DETAINED DISCLOSURE OF THE INVENTION

The present invention relates to novel 5-benzyloxymethyl-1,2-isoxazoline derivatives of the formula 1, their preparation method and their use as herbicides.

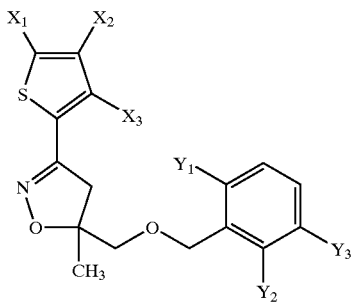

Formula 1 wherein, $X_1$, $X_2$ and $X_3$ represent each independently H, —$CH_3$, —$CH_2CH_3$, a halogen atom, —$OCH_3$ or —$NO_2$ (but, all of $X_1$, $X_2$ and $X_3$ are not H); and $Y_1$, $Y_2$ and $Y_3$ represent each independently H or F.

Preferably, $X_1$ and $X_2$ are independently H, halogen atom or $CH_3$, $X_3$ is H, $CH_3$, a halogen atom, or —$NO_2$; and, at least one of $Y_1$, $Y_2$ and $Y_3$ is F.

Preferable examples of compounds of formula 1 include:

1) 5-benzyloxyl-5-methyl-3-(2-methylthiophene-5-yl)-1,2-isoxazoline (compound of example 1)
2) 5-(2-fluorobenzyl)oxymethyl-5-methyl-3-(2-methylthiophene-5-yl)-1,2-isoxazoline (compound of example 2)
3) 5-(3-fluorobenzyl)oxymethyl-5-methyl-3-(2-methylthiophene-5-yl)-1,2-isoxazoline (compound of example 3)
4) 5-(2,6-difluorobenzyl)oxymethyl-5-methyl-3-(2-methylthiophene-5-yl)-1,2-isoxazoline (compound of example 4)
5) 5-benzyloxymethyl-5-methyl-3-(4-methylthiophene-5-yl)-1,2-isoxazoline (compound of example 5)
6) 5-(2-fluorobenzyl)oxymethyl-5-methyl-3-(4-methylthiophene-5-yl)-1,2-isoxazoline (compound of example 6)
7) 5-(3-fluorobenzyl)oxymethyl-5-methyl-3-(4-methylthiophene-5-yl)-1,2-isoxazoline (compound of example 7)
8) 5-(2,6-difluorobenzyl)oxymethyl-5-methyl-3-(4-methylthiophene-5-yl)-1,2-isoxazoline (compound of example 8)
9) 5-benzyloxymethyl-5-methyl-3-(2-bromothiophene-5-yl)-1,2-isoxazoline (compound of example 9)
10) 5-(3-fluorobenzyl)oxymethyl-5-methyl-3-(2-bromothiophene-5-yl)-1,2-isoxazoline (compound of example 10)
11) 5-(2,6-difluorobenzyl)oxymethyl-5-methyl-3-(2-bromothiophene-5-yl)-1,2-isoxazoline (compound of example 11)
12) 5-benzyloxymethyl-5-methyl-3-(2,4-dimethylthiophene-5-yl)-1,2-isoxazoline (compound of example 12)
13) 5-(2-fluorobenzyl)oxymethyl-5-methyl-3-(2,4-dimethylthiophene-5-yl)-1,2-isoxazoline (compound of example 13)
14) 5-(3-fluorobenzyl)oxymethyl-5-methyl-3-(2,4-dimethylthiophene-5-yl)-1,2-isoxazoline (compound of example 14)
15) 5-(2,6-difluorobenzyl)oxymethyl-5-methyl-3-(2,4-dimethylthiophene-5-yl)-1,2-isoxazoline (compound of example 15)

16) 5-(2-fluorobenzyl)oxymethyl-5-methyl-3-(4-chlorothiophene-5-yl)-1,2-isoxazoline (compound of example 16)
17) 5-(2,6-difluorobenzyl)oxymethyl-5-methyl-3-(4-chlorothiophene-5-yl)-1,2-isoxazoline (compound of example 17)
18) 5-(3-fluorobenzyl)oxymethyl-5-methyl-3-(4-bromothiophene-5-yl)-1,2-isoxazoline (compound of example 18)
19) 5-(2,6-difluorobenzyl)oxymethyl-5-methyl-3-(4-bromothiophene-5-yl)-1,2-isoxazoline (compound of example 19)
20) 5-(3-fluorobenzyl)oxymethyl-5-methyl-3-(4-methoxythiophene-5-yl)-1,2-isoxazoline (compound of example 20)
21) 5-(2,6-difluorobenzyl)oxymethyl-5-methyl-3-(4-methoxythiophene-5-yl)-1,2-isoxazoline (compound of example 21)
22) 5-(2,6-difluorobenzyl)oxymethyl-5-methyl-3-(4-bromo-2-chlorothiophene-5-yl)-1,2-isoxazoline (compound of example 22)
23) 5-(2,6-difluorobenzyl)oxymethyl-5-methyl-3-(2-nitrothiophene-5-yl)-1,2-isoxazoline (compound of example 23)
24) 5-(2,6-difluorobenzyl)oxymethyl-5-methyl-3-(4-methyl-2-nitrothiophene-5-yl)-1,2-isoxazoline (compound of example 24)

The preparation of the compounds of the present invention can be accomplished by a method as shown in scheme 1, comprising:

a) preparing the intermediate compound of formula V by the 1,3-dipolar cycloaddition reaction of the compound of formula III with 2-methyl-2-propene-1-ol of formula IV in the presence of a base; and b) reacting the intermediate compound of formula V with the compound of formula VI in the presence of a base with or without a catalyst.

SCHEME 1

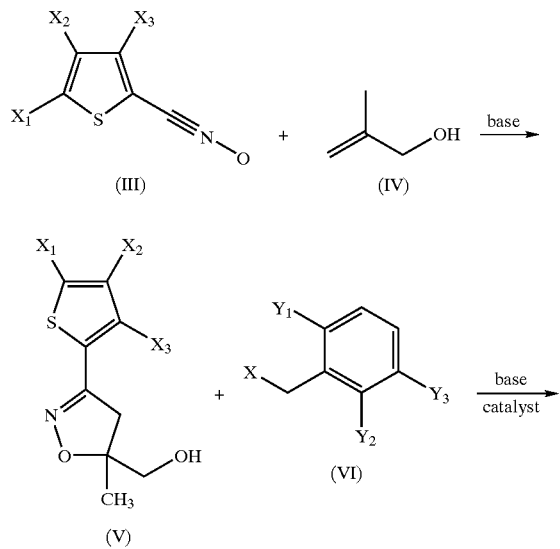

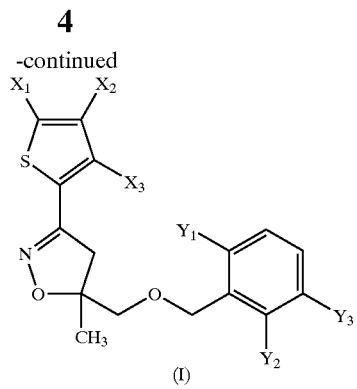

wherein,
$X_1$, $X_2$, $X_3$, $Y_1$, $Y_2$ and $Y_3$ are the same as defined above; and X represents halogen, methanesulfonyloxy, or toluenesulfonyloxy.

A detailed reaction route for the preparation of the 5-benzyloxymethyl-1,2-isoxazoline derivatives of the present invention is described as follows.

Step a): Preparation of the Intermediate Compound V.

In step a) the intermediate compounds of formula V are prepared by the 1,3-dipolar cycloaddition reaction of compound of formula III with 2-methyl-2-propene-1-ol of formula IV.

The reaction is preferably carried out in a suitable organic solvent with a base.

Examples of a suitable base include organic bases such as triethylamine, trimethylamine, diisopropylethylamine, and inorganic bases such as $K_2Co_3$, $CaCO_3$ or $NaCO_3$.

As an organic solvent, but not limited thereto, $C_1$–$C_4$ alcohol, benzene, toluene, tetrahydrofuran, ethyl ether, dimethylformamide and dimethylacetamide can be mentioned.

Step b) Preparation of 5-benzyloxymethyl-1,2-isoxazoline Derivatives.

In step b) the compounds of this invention are prepared by reacting the intermediate compound of formula V with the compound of formula VI.

The reaction is preferably carried out in a suitable organic solvent with a base.

Examples of a suitable base in step b) include metal hydride such as sodium hydride, lithium hydride and calcium hydride; metal alkoxide such as sodium alkoxide and potassium alkoxide; metal amide or metal alkyl amide such as lithium amide and lithium diisopropylamide; and alkyl metal such as t-butyl lithium.

As an organic solvent, the above-mentioned solvent can be also used.

The above reaction can be carried out without a catalyst. Preferable, it is performed in the presence of $I_2$, NaI, KI and tetrabutylammonium iodide.

According to the preferred embodiment of the present invention, the compounds of formula I showed sufficiently high herbicidal activity, particularly, against paddy weeds even at low doses, and excellent selectivity to rice plants, particularly transferred rice. As thus, the compounds of the present invention are useful and safe herbicides, particularly for use in transferred rice. Specifically, the compounds of the present invention showed significantly high herbicidal activity against paddy weeds comprising ECHOR (*Echinochloa crus-galli* var. *oryzicola*), SCPJU (*Scirpus juncoides* ROXB), MOOVA (*Monochoria vaginals* PRESL), CYPSE (*Cyperus serotinus* ROTTB), and SAGPY (*Sagittaria pygmaea* MIQ), in particular, ECHOR and MOOVA. Accordingly, the compounds of the present invention can be effectively used as herbicidal agents against the weeds with strong saftey on paddy rice, and selectivity among rice and paddy weeds, which are compared to known herbicides.

Though the compounds of formula 1 according to the present invention can be used directly in order to control paddy weeds, there is also provided a herbicidal composition comprising an effective amount of the compounds of formula 1 as an effective ingredient and a pharmaceutically acceptable carrier. The herbicidal compositions comprising the compounds of this invention can be formulated in forms such as wettable powder, emulsifiable concentrates, granules, dustable powder, soluble liquid, wettable granules, water dispersible granules, etc.

The herbicidal compositions are preferred to comprise one or more active compounds of the present invention with solid or liquid carriers in formulation.

As a suitable carrier, inorganic powder such as clay, bentonite, montmorylnite, talc, diatomite, mica, gypsum, $CaCO_3$, apatite and silicone hydroxide, organic powder such as soybean flour, wheat flour, sawdust, tobacco, starch and crystalline cellulose, ketone-based polymer resin, alumina and beeswax can be mentioned.

As a suitable liquid carrier, alcohol such as methanol, ethanol, ethylene glycol and benzyl alcohol, aromatic hydrocarbon such as toluene, benzene, xylene and methyl naphthalene; halogenated hydrocarbon such as chloroform and tetrachlomethane; ethers such as dioxane and tetrahydrofuran; ketones such as acetone, methyl ethyl ketone and cyclohexanone; esters such as ethyl acetate, butyl acetate and ethylene glycol acetate; amides such as dimethylformamide; nitrites such as acetonitrile; ether alcohols such as ethylenglycol; diethyl ether, etc.; and water can be mentioned.

As suitable emulsifiers, cationic emulsifiers such as cetyltrimethylammonium bromide; anionic emulsifiers such as alkali metal, alkali earth metal and ammonium salts of alkylarylsulfonic acids, alkyloxysulfonic acids, arylsulfonic acids; and non-ionic emulsifiers such as aliphatic alcohols, caster oil, the condensation products of either naphthalene or naphthalene sulfonic acid with either phenol or formaldehyde.

The herbicidal composition of the present invention may be applied for instance in the form of directly spraying solutions, powders, suspensions, dispersions, emulsions, oil dispersions, pastes or granules by spraying. The forms of application depend entirely on the purpose of which agents are being used.

The composition of the present invention can be formulated as wettable powders, granules or emulsifiable concentrates. These formulations contain preferably from 1 to 50% by weight of the compounds according to the present invention on the basis of the total formulations. In a formulation as liquid hydrate or hydrated granules, the formulations preferably contain from 2 to 40% by weight.

In addition, the compounds of the present invention can be employed in combination with one or more additional known other herbicides, insecticides, fungicides, vermicides, plant-growth regulators, fertilizers, or other agricultural chemicals to improve the herbicidal activity, to broaden the herbicidal spectrum and to achieve synergic eeffects, if necessary. Examples of useful complementary herbicides include 3-isopropyl-1H-2,1,3-benzothiadiazin-4 (3H)one-2,2-dioxide(bentazone), N-(heteroarylamino carbonyl) benzenesulfonic amides such as methyl-2-[3-(4, 6-dimethoxypyrimidin-2-yl)ureidosulfonyl]benzoate (bensufuron -methy, Londax), ethyl-5-[3-(4,6-dimethoxypyrimidin-2-yl)ureidosulfonyl]-1-methylpyrazole-4-carboxylate (pyrazosufuron-ethyl, NC-311), etc.

In addition, the herbicidal compositions of the present invention further comprise one or more additional known herbicides, insecticides, fungicides, vermicides, plant-growth regulators, fertilizers or other agricultural chemicals.

A better understanding of the present invention may be obtained in light of the following examples which are set forth to illustrate, but are not to be construed to limit the present invention.

EXAMPLE 1

Preparation of 5-benzyloxy-5-methyl-3-(2-methyl thiophene-5-yl)-1,2-isoxazoline 1-1) Preparation of 5-hydroxymethyl-5-methyl-3-(2-methylthiophen-5-yl)-1,2-isoxazoline To a solution of 2-methylthiophene-5-carboxaldehyde 1.0 mmol) and hydroxylamine hydrochloride (1.0 mmol) in 30 ml of methanol, 3 mL of aq. NaOH (1.1 mmol) was added dropwise and the mixture was stirred for 1 hr at room temperature. The completion of reaction was checked with thin-layer chromatography (TLC). Addition of 100 mL of an ice-water to the reaction mixture yielded the oxime derivative of 2-methylthiophene-5-carboxaldehyde. The obtained oxime derivative of 2-methylthiophene-5-carboxaldehyde was dried and then was dissolved in 20 mL of dimethylformamide. To this solution, N-chlorosuccinimide (1.0 mmol) was added dropwise at room temperature and stirred for another 1 hr. After the completion of the reaction, the reaction mixture was poured into 100 mL of an ice-water, and then extracted with 100 mL of dichloromethane. The organic layer was washed with 50 mL aqueous NaCl solution, and then dried over anhydrous magnesium sulfate ($MgSO_4$). The filtrate was concentrated under reduced pressure. The obtained residue (2-methylthiophene-5-carboxaldehyde hydroxymoyl chloride) was dissoved in dichloromethane (200 mL). The solution was added to a solution of 2-methyl-2-propene-1-ol (2.0 mmol) in dimethylforamide with triethylamine (1 mmol) and the mixture stirred for 0.5 hr. After the completion of reaction, the reaction mixture was poured into 100 mL of an ice-water and extracted with 150 mL of dichloromethane. The organic layer was washed with aqueous NaCl solution, dried over anhydrous $MgSO_4$ and then concentrated under reduced pressure. The residue was purified by silica-gel column chromatography (ethyl acetate:n-hexane=1:5, v/v) to give 5-hydroxymethyl-5-methyl-3-(2-methylthiophen-5-yl)-1,2-isoxazoline.

1-2) Preparation of 5-benzyloxyl-5-methyl-3-(2-methylthiophene-5-yl)-1,2-isoxazoline To a solution of 5-hydroxymethyl-5-methyl-3-(2-methylthiophen-5-yl)-1,2-isoxazoline (1.0 mmol) in dimethylformamide (20 mL) was added sodium hydride slowly and stirred for 0.5 hr at 0° C. To this solution, a solution of benzylchloride (1.1 mmol) in dimethylformamide was added dropwise and stirred for another 2 hrs. After the completion of reaction, the reaction mixture was poured into 100 mL of an ice-water, extracted with 150 mL of dichloromethane. The organic layer was washed with aqueous NaCl solution, dehydrated over anhydrous $MgSO_4$ and then concentrated under reduced pressure.

The residue was purified by silica-gel column chromatography (ethyl acetate:hexane=1:5, v/v) to afford the desired 5-benzyloxyl-5-methyl-3-(2-methyl thiophene-5-yl)-1,2-isoxazoline.

$^1$H NMR (CDCl$_3$): δ1.46(s, 3H), 2.48(s, 3H), 2.95(d, 1H, J=16.5 Hz), 3.40(d, 1H, J=16.5 Hz), 3.52(dd, 2H, J=10.0, 13.0 Hz), 4.60(s, 2H), 6.68(d, 1H, J=3.5 Hz), 6.93(d, 1H, J=3.5 Hz), 7.24–7.36(m, 5H)

EXAMPLE 2

Preparation of 5-(2-fluorobenzyl)oxymethyl-5-methyl-3-(2-methylthiophene-5-yl)-1,2-isoxazoline The desired product was prepared in the same manner described in Example 1, except that 2-fluorobenzyl chloride was used instead of benzyl chloride.

$^1$H NMR (CDCl$_3$): δ 1.46(s, 3H), 2.48(s, 3H), 2.96(d, 1H, J=16.5 Hz), 3.41(d, 1H, J=16.5 Hz), 3.55(dd, 2H, J=10.0, 14.0 Hz), 4.66(s, 2H), 6.67–6.70(m, 1H), 7.01–7.39(m, 5H)

EXAMPLE 3

Preparation of 5-(3-fluorobenzyl)oxymethyl-5-methyl-3-(2-methylthiophene-5-yl)-1,2-isoxazoline The desired product was prepared in the same manner described in Example 1, except that 3-fluorobenzyl chloride was used instead of benzyl chloride.

$^1$H NMR (CDCl$_3$): δ 1.45(s, 3H), 2.47(s, 3H), 2.95(d, 1H, J=16.5 Hz), 3.40(d, 1H, J=16.5 Hz), 3.54(dd, 2H, J=10.0, 13.8 Hz), 4.65(s, 2H), 6.68(d, 1H, J=3.5 Hz), 6.93(d, 1H, J=3.5 Hz), 6.92–7.41(m, 4H)

EXAMPLE 4

Preparation of 5-(2,6-difluorobenzyl)oxymethyl-5-methyl-3-(2-methylthiophene-5-yl)-1,2-isoxazoline The desired product was prepared in the same manner described in Example 1, except that 2,6-difluorobenzyl chloride was used instead of benzyl chloride.

$^1$H NMR (CDCl$_3$): δ 1.46(s, 3H), 2.48(s, 3H), 2.96(d, 1H, J=16.5 Hz),3.41(d, 1H, J=16.5 Hz), 3.55(dd, 2H, J=10.0, 14.0 Hz), 4.66(s, 2H), 6.67–6.70(m, 1H), 7.01–7.39(m, 5H)

EXAMPLE 5

Preparation of 5-benzyloxymethyl-5-methyl-3-(4-methylthiophene-5-yl)-1,2-isoxazoline The desired product was prepared in the same manner described in Example 1, except that 3-methylthiophene-2-carboxaldehyde was used instead of 2-methylthiophene-5-carboxaldehyde.

$^1$H NMR (CDCl$_3$): δ 1.45(s, 3H), 2.43(s, 3H), 3.00(d, 1H, J=16.5 Hz), 3.44(d, 1H, J=16.5 Hz), 3.51(dd, 2H, J=10.0, 14.2 Hz), 4.59(s, 2H), 6.86(d, 1H, J=5.1 Hz), 7.22(d, 1H, J=5.1 Hz), 7.23–7.33(m, 5H)

EXAMPLE 6

Preparation of 5-(2-fluorobenzyl)oxymethyl-5-methyl-3-(4-methylthiophene-5-yl)-1,2-isoxazoline The desired product was prepared in the same manner described in example 1, except that 3-methylthiophene-2-carboxaldehyde and 2-fluorobenzyl chloride were used instead of 2-methylthiophene-5-carbozaldehyde and benzyl chloride, respectively.

$^1$H NMR (CDCl$_3$): δ 1.47(s, 3H), 2.45(s, 3H), 3.02(d, 1H, J=16.5 Hz), 3.46(d, 1H, J=16.5 Hz), 3.57(dd, 2H, J=10.0, 15.4 Hz), 4.67(s, 2H), 6.88–7.43(m, 6H)

EXAMPLE 7

Preparation of 5-(3-fluorobenzyl)oxymethyl-5-methyl-3-(4-methylthiophene-5-yl)-1,2-isoxazoline The desired product was prepared in the same manner described in Example 1, except that 3-methylthiophene-2-carboxaldehyde and fluorobenzyl chloride were used instead of 2-methylthiophene-5-carbozaldehyde and benzyl chloride, respectively.

$^1$H NMR (CDCl$_3$): δ 1.46(s, 3H), 2.44(s, 3H), 2.99(d, 1H, J=16.5 Hz), 3.44(d, 1H, J=16.5 Hz), 3.53(dd, 2H, J=10.0, 13.2 Hz), 4.58(s, 2H), 6.85–7.27 (m, 6H)

EXAMPLE 8

Preparation of 5-(2,6-fluorobenzyl)oxymethyl-5-methyl-3-(4-methylthiophene-5-yl)-1,2-isoxazoline The desired product was prepared in the same manner described in Example 1, except that 3-methylthiophene-2-carboxaldehyde and 2,6-difluorobenzyl chloride were used instead of 2-methylthiophene-5-carboxaldehyde and benzyl chloride, respectively.

$^1$H NMR (CDCl$_3$): δ 1.42(s, 3H), 2.41(s, 3H), 2.95(d, 1H, J=16.5 Hz), 3.41(d, 1H, J=16.5 Hz), 3.53(dd, 2H, J=10.0, 15.9 Hz), 4.68(s, 2H), 6.82–6.89(m, 6H), 7.20–7.25(m, 2H)

EXAMPLE 9

Preparation of 5-benzyloxymethyl-5-methyl-3-(2-bromothiophene-5-yl)-1,2-isoxazoline The desired product was prepared in the same manner described in Example 1, except that 5-bromothiophene-2-carboxaldehyde was used instead of 2-methylthiophene-5-carbozaldehyde.

$^1$H NMR (CDCl$_3$): δ 1.46(s, 3H), 2.92(d, 1H, J=16.5 Hz), 3.39(d, 1H, J=16.5 Hz), 3.51(dd, 2H, J=10.2, 14.0 Hz), 4.59(s, 2H), 6.85(d, 1H, J=3.8 Hz), 6.98(d, 1H, J=3.8 Hz), 7.24–7.35(m, 5H)

EXAMPLE 10

Preparation of 5-(3-fluorobenzyl)oxymethyl-5-methyl-3-(2-bromothiophene-5-yl)-1,2-isoxazoline The desired product was prepared in the same manner described in Example 1, except that 5-bromothiophene-2-carboxaldehyde and 3-fluorobenzyl chloride were used instead of 2-methylthiophene-5-carbozaldehyde and benzyl chloride, respectively.

$^1$H NMR (CDCl$_3$): δ 1.48(s, 3H), 2.96(d, 1H, J=16.7 Hz), 3.41(d, 1H, J=16.7 Hz), 3.55(dd, 2H, J=10.2, 13.4 Hz), 4.60(s, 2H), 6.87–7.10(m, 5H), 7.24–7.35(m, 6H)

EXAMPLE 11

Preparation of 5-(2,6-difluorobenzyl)oxymethyl-5-methyl-3-(2-bromothiophene-5-yl)-1,2-isoxazoline The desired product was prepared in the same manner described in Example 1, except for using 5-bromothiophene-2-carboxaldehyde and 2,6-difluorobenzyl chloride were used instead of 2-methylthiophene-5-carbozaldehyde and benzyl chloride, respectively.

¹H NMR (CDCl₃): δ 1.45(s, 3H), 2.90(d, 1H, J=16.7 Hz), 3.37 (d, 1H, J=16.7 Hz), 3.54(dd, 2H, J=10.2, 15.8 Hz), 4.69(s, 2H), 6.82–7.00(m, 4H), 7.20–7.32(m, 6H)

EXAMPLE 12

Preparation of 5-benzyloxymethyl-5-methyl-3-(2,4-dimethylthiophene-5-yl)-1,2-isoxazoline The desired product was prepared in the same manner described in Example 1, except that 3,5-dimethylthiophene-2-carboxaldehyde was used instead of 2-methylthiophene-5-carbozaldehyde.

¹H NMR (CDCl₃): δ 1.45(s, 3H), 2.36(s, 3H), 2.43(s, 3H), 2.97(d, 1H, J=16.5 Hz), 3.41(d, 1H, J=16.5 Hz), 3.52(dd, 2H, J=10.0, 13.2 Hz), 4.61(s, 2H), 6.57(s, 1H), 7.26–7.34(m, 5H)

EXAMPLE 13

Preparation of 5-(2-fluorobenzyl)oxymethyl-5-methyl-3-(2,4-dimethylthiophene-5-yl)-1,2-isoxazoline The desired product was prepared in the same manner described in Example 1, except that 3,5-dimethylthiophene-2-carboxaldehyde and 2-fluorobenzyl chloride were used instead of 2-methylthiophene-5-carbozaldehyde and benzyl chloride, respectively.

¹H NMR (CDCl₃): δ 1.45(s, 3H), 2.35(s, 3H), 2.42(s, 3H), 2.97(d, 1H, J=17.3 Hz), 3.55(dd, 2H, J=10.0, 14.8 Hz), 4.67 (s, 2H), 6.56(s, 1H), 6.97–7.40(m, 4H)

EXAMPLE 14

Preparation of 5-(3-fluorobenzyl)oxymethyl-5-methyl-3-(2,4-dimethylthiophene-5-yl)-1,2-isoxazoline The desired product was prepared in the same manner described in Example 1, except that 3,5-dimethylthiophene-2-carboxaldehyde and 3-fluorobenzyl chloride were used instead of 2-methylthiophene-5-carbozaldehyde and benzyl chloride, respectively.

¹H NMR (CDCl₃): δ 1.46(s, 3H), 2.36(s, 3H), 2.42(s, 3H), 2.98(d, 1H, J=16.5 Hz), 3.40(d, 1H, J=16.5 Hz), 3.53(dd, 2H, J=10.1, 13.6 Hz), 4.59(s, 2H), 6.56(s, 1H), 6.93–7.09(m, 3H), 7.22–7.30(m, 1H)

EXAMPLE 15

Preparation of 5-(2,6-difluorobenzyl)oxymethyl-5-methyl-3-(2,4-dimethylthiophene-5-yl)-1,2-isoxazoline The desired product was prepared in the same manner described in Example 1, except that 3,5-dimethylthiophene-2-carboxaldehyde and 2,6-difluorobenzyl chloride were used instead of 2-methylthiophene-5-carbozaldehyde and benzyl chloride, respectively.

¹H NMR (CDCl₃): δ 1.43(s, 3H), 2.35(s, 3H), 2.42(s, 3H), 2.93(d, 1H, J=16.5 Hz), 3.38(d, 1H, J=16.5 Hz), 3.53(dd, 2H, J=10.0, 15.7 Hz), 4.69(s, 2H), 6.55(s, 1H), 6.84–6.92(m, 2H), 7.22–7.27(m, 1H)

EXAMPLE 16

Preparation of 5-(2-fluorobenzyl)oxymethyl-5-methyl-3-(4-chlorothiophene-5-yl)-1,2-isoxazoline The desired product was prepared in the same manner described in Example 1, except that 3-chlorothiophene-2-carboxaldehyde and 2-fluorobenzyl chloride were used instead of 2-methylthiophene-5-carbozaldehyde and benzyl chloride, respectively.

¹H NMR (CDCl₃): δ 1.43(s, 3H), 2.88(d, 1H, J=16.5 Hz), 3.39 (d, 1H, J=16.5 Hz), 3.51(dd, 2H, J=10.0, 15.9 Hz), 4.65(s, 2H), 6.75–7.11(m, 6H)

EXAMPLE 17

Preparation of 5-(2,6-difluorobenzyl)oxymethyl-5-methyl-3-(4-chlorothiophene-5-yl)-1,2-isoxazoline The desired product was prepared in the same manner described in Example 1, except that 3-chlorothiophene-2-carboxaldehyde and 2,6-difluorobenzyl chloride were used instead of 2-methylthiophene-5-carbozaldehyde and benzyl chloride, respectively.

¹H NMR (CDCl₃): δ 1.42(s, 3H), 2.88(d, 1H, J=16.5 Hz), 3.38 (d, 1H, J=16.5 Hz), 3.51(dd, 2H, J=10.0, 15.9 Hz), 4.66(s, 2H), 6.85–7.20(m, 5H)

EXAMPLE 18

Preparation of 5-(3-fluorobenzyl)oxymethyl-5-methyl-3-(4-bromothiophene-5-yl)-1,2-isoxazoline The desired product was prepared in the same manner described in Example 1, except that 3-bromothiophene-2-carboxaldehyde and 3-fluorobenzyl chloride were used instead of 2-methylthiophene-5-carbozaldehyde and benzyl chloride, respectively.

¹H NMR (CDCl₃): δ 1.57(s, 3H), 3.28(d, 1H, J=17.1 Hz), 3.69 (d, 1H, J=17.1 Hz), 3.55(dd, 2H, J=10.2, 15.7 Hz), 4.61(s, 2H), 6.98–7.06(m, 3H), 7.25–7.30(m, 3H)

EXAMPLE 19

Preparation of 5-(2,6-difluorobenzyl)oxymethyl-5-methyl-3-(4-bromothiophene-5-yl)-1,2-isoxazoline The desired product was prepared in the same manner described in Example 1, except that 3-bromothiophene-2-carboxaldehyde and 2,6-difluorobenzyl chloride were used instead of 2-methylthiophene-5-carbozaldehyde and benzyl chloride, respectively.

¹H NMR (CDCl₃): δ 1.45(s, 3H), 3.22 (d, 1H, J=17.3 Hz), 3.65 (d, 1H, J=17.3 Hz), 3.55(dd, 2H, J=10.0, 14.2 Hz), 4.70(s, 2H), 6.84–6.99(m, 3H), 7.23–7.29(m, 2H)

EXAMPLE 20

Preparation of 5-(3-fluorobenzyl)oxymethyl-5-methyl-3-(4-methoxythiophene-5-yl)-1,2-isoxazoline The desired product was prepared in the same manner described in Example 1, except that 3-methoxythiophene-2-carboxaldehyde and 3-fluorobenzyl chloride were used instead of 2-methylthiophene-5-carbozaldehyde and benzyl chloride, respectively.

¹H NMR (CDCl₃): δ 1.45(s, 3H), 3.12(d, 1H, J=17.3 Hz), 3.51 (d, 1H, J=17.3 Hz), 3.52(dd, 2H, J=10.0, 15.7 Hz), 3.86(s, 3H), 4.59(s, 2H), 6.79–7.29(m, 6H)

EXAMPLE 21

Preparation of 5-(2,6-difluorobenzyl)oxymethyl-5-methyl-3-(4-methoxythiophene-5-yl)-1,2-isoxazoline The desired product was prepared in the same manner described in Example 1, except that 3-methoxythiophene- 2-carboxaldehyde and 2,6-difluorobenzyl chloride were used instead of 2-methylthiophene-5-carbozaldehyde and benzyl chloride, respectively.

$^1$H NMR (CDCl$_3$): δ 1.42(s, 3H), 3.08(d, 1H, J=17.3 Hz), 3.47 (d, 1H, J=17.3 Hz), 3.53(dd, 2H, J=10.1, 14.2 Hz), 3.87(s, 3H), 4.70(s, 2H), 6.80–6.92(m, 3H), 7.21–7.26(m, 2H)

EXAMPLE 22

Preparation of 5-(2,6-difluorobenzyl)oxymethyl-5-methyl-3-(4-bromo-2-chlorothiophene-5-yl)-1,2-isoxazoline The desired product was prepared in the same manner described in Example 1, except that 3-bromo-5-chlorothiophene-2-carboxaldehyde and 2,6-difluorobenzyl chloride were used instead of 2-methylthiophene-5-carbozaldehyde and benzyl chloride, respectively.

$^1$H NMR (CDCl$_3$): δ 1.43(s, 3H), 2.89(d, 1H, J=16.5 Hz), 3.36 (d, 1H, J=16.5 Hz), 3.53(dd, 2H, J=10.0, 15.9 Hz), 4.68(s, 2H), 6.85–7.31(m, 4H)

EXAMPLE 23

Preparation of 5-(2,6-difluorobenzyl)oxymethyl-5-methyl-3-(2-nitrothiophene-5-yl)-1,2-isoxazoline The desired product was prepared in the same manner described in Example 1, except that 5-nitrothiophene-2-carboxaldehyde and 2,6-difluorobenzyl chloride were used instead of 2-methylthiophene-5-carbozaldehyde and benzyl chloride, respectively.

$^1$H NMR (CDCl$_3$): δ 1.46(s, 3H), 2.92(d, 1H, J=16.4 Hz), 3.42 (d, 1H, J=16.4 Hz), 3.57(dd, 2H, J=10.1, 19.5 Hz), 4.68(dd, 2H, J=9.3, 12.3 Hz), 6.88(t, 2H, J=7.3 Hz), 7.05(d, 1H, J=4.3 Hz), 7.21–7.33(m, 1H), 7.84(d, 1H, J=4.3 Hz)

EXAMPLE 24

Preparation of 5-(2,6-difluorobenzyl)oxymethyl-5-methyl-3-(4-methyl-2-nitrothiophene-5-yl)-1,2-isoxazoline The desired product was prepared in the same manner described in Example 1, except that 3-methyl-5-nitrothiophene-2-carboxaldehyde and 2,6-difluorobenzyl chloride were used instead of 2-methylthiophene-5-carbozaldehyde and benzyl chloride, respectively.

$^1$H NMR (CDCl$_3$): δ 1.45(s, 3H), 2.43(s, 3H), 2.93(d, 1H, J=16.7 Hz), 3.42(d, 1H, J=16.5 Hz), 3.56(dd, 2H, J=10.2, 20.9 Hz), 4.68(dd, 2H, J=11.2, 14.8 Hz), 6.88(t, 2H, J=7.5 Hz), 7.20–7.35 (m, 1H), 7.69(s, 1H)

The herbicidal activity of the compounds of formula I is demonstrated in a greenhouse and the typical test examples are given below.

Experimental Example 1

Assay for Herbicidal Activity

To evaluate herbicidal activity against the paddy weeds in the paddy rice (ORYSA: *Oryza sativa* L.), the herbicidal activity of the compounds of the invention was compared to that of the compound No.109 (compound A) disclosed in U.S. Pat. No. 4,983,210 which has a similar structure with that of the present invention. The paddy weeds tested were ECHOR (*Echinochloa crus-galli* var. *oryzicola*), SCPJU (*Scirpus juncoides* ROXB), MOOVA (*Monochoria vaginalis* PRESL), CYPSE (*Cyperus serotinus* ROTTB), and SAGPY (*Sagittaria pygmaea* MTQ).

The vessels employed were plastic pots having an area of 140 cm$^2$ and filled with a sandy loam soil containing 1.2% organic matter (pH 6). Rice seedlings at the 3-leaf stage (ORYSA: *Oryza sativa* L.) and pregerminated seeds of rice were transplanted at the depth of 2 cm or seeded on the soil surface, respectively. Then the seeds of ECHOR, SCPJU, and MOOVA were seeded and the tubers of CYPSE and SAGPY also planted on the soil surface in the above plastic pot, wherein the pots were watered at the depth of 3 cm just after planting.

Two days after planting, a solution of the test compound and a non-ionic emulsifier (Tween-20) in 50% acetone, was diluted with water to a concentration of 0.016, 0.063, 0.25, 1.0, and 4.0 kg/ha, respectively and applied evenly to the test pots.

Three weeks after the application of the herbicide, the herbicidal activity on paddy weeds and the phytotoxicity to the paddy rice plant were visually rated by a percentage grading wherein 0 indicates as an untreated control and 100 indicates complete kill. The results are shown in the following Table 1.

TABLE 1

| Compound | Conc. (kg/ha) | ORYSA (3-leaf stage) | ORYSA (seed) | ECHOR (seed) | SCPJU (seed) | MOOVA (seed) | CYPSE (tuber) | SAGPY (tuber) |
|---|---|---|---|---|---|---|---|---|
| EXAMPLE 3 | 4.000 | 40 | 100 | 100 | 100 | 100 | 100 | 40 |
|  | 1.000 | 20 | 100 | 100 | 60 | 80 | 100 | 50 |
|  | 0.250 | 10 | 100 | 100 | 40 | 60 | 90 | 0 |
|  | 0.063 | 0 | 40 | 55 | 20 | 50 | 40 | 0 |
|  | 0.016 | 0 | 20 | 20 | 0 | 20 | 0 | 0 |
| EXAMPLE 5 | 4.000 | 70 | 100 | 100 | 100 | 100 | 100 | 70 |
|  | 1.000 | 0 | 100 | 100 | 60 | 90 | 100 | 50 |
|  | 0.250 | 0 | 100 | 100 | 30 | 80 | 30 | 20 |
|  | 0.063 | 0 | 10 | 30 | 10 | 10 | 0 | 0 |
|  | 0.016 | 0 | 0 | 0 | 0 | 0 | 0 | 0 |
| EXAMPLE 6 | 4.000 | 30 | 100 | 100 | 100 | 100 | 100 | 30 |
|  | 1.000 | 30 | 100 | 100 | 100 | 80 | 100 | 30 |
|  | 0.250 | 20 | 100 | 100 | 80 | 80 | 100 | 0 |
|  | 0.063 | 20 | 40 | 100 | 80 | 70 | 100 | 0 |
|  | 0.016 | 0 | 0 | 20 | 20 | 0 | 100 | 0 |
| EXAMPLE 8 | 4.000 | 90 | 100 | 100 | 100 | 100 | 100 | 80 |
|  | 1.000 | 20 | 100 | 100 | 40 | 100 | 100 | 50 |

TABLE 1-continued

| Compound | Conc. (kg/ha) | ORYSA (3-leaf stage) | ORYSA (seed) | ECHOR (seed) | SCPJU (seed) | MOOVA (seed) | CYPSE (tuber) | SAGPY (tuber) |
|---|---|---|---|---|---|---|---|---|
|  | 0.250 | 0 | 100 | 100 | 10 | 90 | 90 | 0 |
|  | 0.063 | 0 | 30 | 100 | 10 | 90 | 50 | 0 |
|  | 0.016 | 0 | 10 | 50 | 0 | 50 | 0 | 0 |
| EXAMPLE 11 | 4.000 | 0 | 100 | 100 | 80 | 100 | 100 | 50 |
|  | 1.000 | 0 | 100 | 100 | 30 | 100 | 100 | 30 |
|  | 0.250 | 0 | 100 | 100 | 20 | 90 | 40 | 0 |
|  | 0.063 | 0 | 0 | 70 | 0 | 50 | 0 | 0 |
|  | 0.016 | 0 | 0 | 20 | 0 | 30 | 0 | 0 |
| EXAMPLE 13 | 4.000 | 40 | 100 | 100 | 100 | 100 | 100 | 30 |
|  | 1.000 | 20 | 100 | 100 | 90 | 90 | 100 | 0 |
|  | 0.250 | 20 | 100 | 100 | 70 | 80 | 90 | 0 |
|  | 0.063 | 0 | 40 | 70 | 30 | 70 | 0 | 0 |
|  | 0.016 | 0 | 0 | 50 | 30 | 50 | 0 | 0 |
| EXAMPLE 15 | 4.000 | 100 | 100 | 100 | 100 | 100 | 100 | 70 |
|  | 1.000 | 60 | 100 | 100 | 100 | 100 | 100 | 40 |
|  | 0.250 | 10 | 100 | 100 | 100 | 100 | 70 | 20 |
|  | 0.063 | 0 | 40 | 100 | 50 | 100 | 0 | 0 |
|  | 0.016 | 0 | 0 | 40 | 20 | 90 | 0 | 0 |
| EXAMPLE 18 | 4.000 | 0 | 100 | 100 | 100 | 100 | 100 | 20 |
|  | 1.000 | 0 | 100 | 100 | 100 | 100 | 100 | 0 |
|  | 0.250 | 0 | 100 | 100 | 100 | 100 | 70 | 0 |
|  | 0.063 | 0 | 100 | 60 | 10 | 100 | 40 | 0 |
|  | 0.016 | 0 | 100 | 0 | 0 | 0 | 0 | 0 |
| EXAMPLE 19 | 4.000 | 90 | 100 | 100 | 100 | 100 | 100 | 30 |
|  | 1.000 | 70 | 100 | 100 | 100 | 100 | 100 | 20 |
|  | 0.250 | 30 | 100 | 100 | 100 | 100 | 90 | 0 |
|  | 0.063 | 0 | 40 | 100 | 100 | 95 | 90 | 0 |
|  | 0.016 | 0 | 20 | 100 | 0 | 20 | 30 | 0 |
| EXAMPLE 21 | 4.000 | 95 | 100 | 100 | 100 | 100 | 100 | 0 |
|  | 1.000 | 50 | 100 | 100 | 100 | 100 | 80 | 0 |
|  | 0.250 | 40 | 100 | 100 | 100 | 100 | 60 | 0 |
|  | 0.063 | 0 | 30 | 100 | 100 | 100 | 40 | 0 |
|  | 0.016 | 0 | 0 | 0 | 0 | 0 | 0 | 0 |
| EXAMPLE 23 | 4.000 | 20 | 100 | 100 | 100 | 100 | 100 | 0 |
|  | 1.000 | 0 | 100 | 100 | 0 | 100 | 80 | 0 |
|  | 0.250 | 0 | 70 | 100 | 0 | 70 | 50 | 0 |
|  | 0.063 | 0 | 10 | 30 | 0 | 50 | 0 | 0 |
|  | 0.016 | 0 | 0 | 0 | 0 | 0 | 0 | 0 |
| Compound A | 4.000 | 0 | 100 | 100 | 100 | 100 | 100 | 100 |
|  | 1.000 | 0 | 100 | 100 | 70 | 80 | 100 | 100 |
|  | 0.250 | 0 | 20 | 20 | 10 | 80 | 10 | 100 |
|  | 0.063 | 0 | 0 | 0 | 0 | 0 | 0 | 0 |
|  | 0.016 | 0 | 0 | 0 | 0 | 0 | 0 | 0 |

In the Table 1, the compound A was prepared according to U.S. Pat. No. 4,983,210 in order to compare the herbicidal activity as a Reference, whose structure is represented by the Compound A.

Compound A

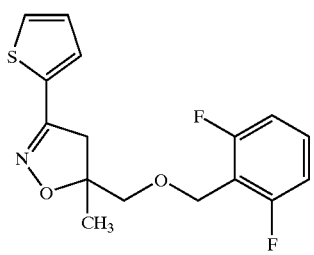

As can be seen from the results, the compounds of the present invention showed superior herbicidal activity against the paddy weeds even at the low dose than that of compound A, together with the excellent tolerance on the transplanted rice, in particular.

Experimental Example 2

Assay for Herbicidal Activity on the 2-leaf Stage Weeds and Rice Plants

The vessels employed were plastic pots having an area of 140 cm$^2$ and filled with a sandy loam soil containing 1.2% organic matter (pH 6). Pregerminated seed of rice (ORYSA: *Oryza sativa* L.) and seed of ECHOR (*Echinochloa crusgalli* var *oryzicola*) were seeded on the soil surface, respectively. The pots were then watered at the depth of 3 cm just after seeding.

Seven days after seeding, the pregerminated seeds of rice were seeded on the soil face whilst the early seeded rice in the same pots and barnyard grass (ECHOR) grew up to the 2-leaf stage. Two days after, a solution of the compound of Example 8 and Tween-20 as a non-ionic emulsifier in 50% acetone, was diluted with water to a concentration of 0.016, 0.063, 0.25, 1 and 4.0 kg/ha, respectively and applied evenly to the test pots.

Three weeks after starting from the beginning, the application of the herbicide, the herbicidal activity on paddy weeds and the phytotoxicity to the paddy rice plant were visually rated by a percentage grading wherein 0 indicates as an untreated control and 100 indicates complete kill. The results are shown in the following

TABLE 2

| Conc. Of | ORYSA | | ECHOR |
|---|---|---|---|
| compound (kg/ha) | 2-leaf stage | seed | 2-leaf stage |
| 4.000 | 65 | 95 | 100 |
| 1.000 | 20 | 80 | 100 |
| 0.250 | 0 | 55 | 100 |
| 0.063 | 0 | 20 | 95 |
| 0.016 | 0 | 0 | 45 |

As apparent from the results of Table 1 and 2, the compounds of the present invention did not adversely affects the growth of transplanted ORYSA up to the dose of 1.0 kg/ha, and showed a very good herbicidal activity on ECHOR at the low dose of 0.063 to 0.250 Kg/ha. Furthermore, the compounds according to the present invention showed sufficiently high herbicidal activity against the various paddy weeds such as SCPJU, MOOVA, CYPSE, LUDPR (*Ludwigia prostrata* ROXB), CYPDI (*Cyprus diffomis* L.), ROTIN (*Rotala indica* KOEHE), LIDPY (*Lindernia pyxidaria* L.), SAGPY, etc.

In particular, the compound of Example 19 has the significantly high herbicidal activity at the low dose of 0.016 Kg/ha, which completely controls the growth of ECHOR. In contrast, compound A disclosed in U.S. Pat. No. 4,983,210, although active at the higher doses, is inactive at the lower doses. As thus, the compounds of the present invention have shown an excellent level of herbicidal activity together with rice tolerance on the paddy weeds used in the foregoing experiments and can be used as the useful and the safe herbicides.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:
1. Derivatives of 5-benzyloxymethyl-1,2-isoxazoline having the formula 1:

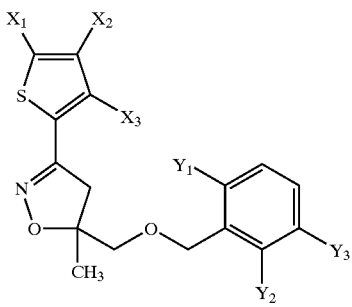

Formula 1 wherein,
$X_1$, $X_2$, $X_3$ represent each independently H, $CH_3$, $CH_2CH_3$, a halogen atom, $OCH_3$ or $NO_2$ (but, all of $X_1$, $X_2$ and $X_3$ are not H); and
$Y_1$, $Y_2$ and $Y_3$ represent each independently H or F.

2. The derivatives according to claim 1, wherein $X_1$ and $X_2$ are independently H, halogen atom, H, or $CH_3$, $X_3$ is $CH_3$, a halogen atom, or $NO_2$; and, at least one of $Y_1$, $Y_2$ and $Y_3$ is F.

3. The derivatives according to claim 1, wherein the derivatives are selected from the group consisting of:
1) 5-benzyloxy-5-methyl-3-(2-methylthiophene-5-yl)-1,2-isoxazoline;
2) 5-(2-fluorobenzyl)oxymethyl-5-methyl-3-(2-methylthiophene-5-yl)-1,2-isoxazoline;
3) 5-(3-fluorobenzyl)oxymethyl-5-methyl-3-(2-methylthiophene-5-yl)-1,2-isoxazoline;
4) 5-(2,6-difluorobenzyl)oxymethyl-5-methyl-3-(2-methylthiophene-5-yl)-1,2-isoxazoline;
5) 5-benzyloxymethyl-5-methyl-3-(4-methylthiophene-5-yl)-1,2-isoxazoline;
6) 5-(2-fluorobenzyl)oxymethyl-5-methyl-3-(4-methylthiophene-5-yl)-1,2-isoxazoline;
7) 5-(3-fluorobenzyl)oxymethyl-5-methyl-3-(4-methylthiophene-5-yl)-1,2-isoxazoline;
8) 5-(2,6-difluorobenzyl)oxymethyl-5-methyl-3-(4-methylthiophene-5-yl)-1,2-isoxazoline;
9) 5-benzyloxymethyl-5-methyl-3-(2-bromothiophene-5-yl)-1,2-isoxazoline;
10) 5-(3-fluorobenzyl)oxymethyl-5-methyl-3-(2-bromothiophene-5-yl)-1,2-isoxazoline;
11) 5-(2,6-difluorobenzyl)oxymethyl-5-methyl-3-(2-bromothiophene-5-yl)-1,2-isoxazoline;
12) 5-benzyloxymethyl-5-methyl-3-(2,4-dimethylthiophene-5-yl)-1,2-isoxazoline;
13) 5-(2-fluorobenzyl)oxymethyl-5-methyl-3-(2,4-dimethylthiophene-5-yl)-1,2-isoxazoline;
14) 5-(3-fluorobenzyl)oxymethyl-5-methyl-3-(2,4-dimethylthiophene-5-yl)-1,2-isoxazoline;
15) 5-(2,6-difluorobenzyl)oxymethyl-5-methyl-3-(2,4-dimethylthiophene-5-yl)-1,2-isoxazoline;
16) 5-(2-fluorobenzyl)oxymethyl-5-methyl-3-(4-chlorothiophene-5-yl)-1,2-isoxazoline;
17) 5-(2,6-difluorobenzyl)oxymethyl-5-methyl-3-(4-chlorothiophene-5-yl)-1,2-isoxazoline;
18) 5-(3-fluorobenzyl)oxymethyl-5-methyl-3-(4-bromothiophene-5-yl)-1,2-isoxazoline;
19) 5-(2,6-difluorobenzyl)oxymethyl-5-methyl-3-(4-bromothiophene-5-yl)-1,2-isoxazoline;
20) 5-(3-fluorobenzyl)oxymethyl-5-methyl-3-(4-methoxythiophene-5-yl)-1,2-isoxazoline;
21) 5-(2,6-difluorobenzyl)oxymethyl-5-methyl-3-(4-methoxythiophene-5-yl)-1,2-isoxazoline;
22) 5-(2,6-difluorobenzyl)oxymethyl-5-methyl-3-(4-bromo-2-chlorothiophene-5-yl)-1,2-isoxazoline;
23) 5-(2,6-difluorobenzyl)oxymethyl-5-methyl-3-(2-nitrothiophene-5-yl)-1,2-isoxazoline; and,
24) 5-(2,6-difluorobenzyl)oxymethyl-5-methyl-3-(4-methyl-2-nitrothiophene-5-yl)-1,2-isoxazoline.

4. The derivatives according to claim 1, wherein they have an herbicidal activity against the weeds including ECHOR (*Echinochloa crus-galli* var. *oryzicola*), SCPJU (*Scirpus juncoides* ROXB), MOOVA (*Monochoria vaginalis* PRESL), CYPSE (*Cyperus serotinus* ROTTB), and SAGPY (*Sagittaria pygmaea* MTQ) in the paddy field rice crops.

5. A process for preparing said derivatives of 5-benzyloxymethyl-1,2-isoxazoline according to claim 1 comprising the following steps of:
a) preparing intermediate compound of formula V by the 1,3-dipolar cycloaddition reaction of the compound of the formula III with 2-methyl-2-propene-1-ol of the formula IV in the presence of a base; and
b) reacting the intermediate compound of formula V with compound of formula VI in the presence of a base with or without a catalyst,

SHEME 1

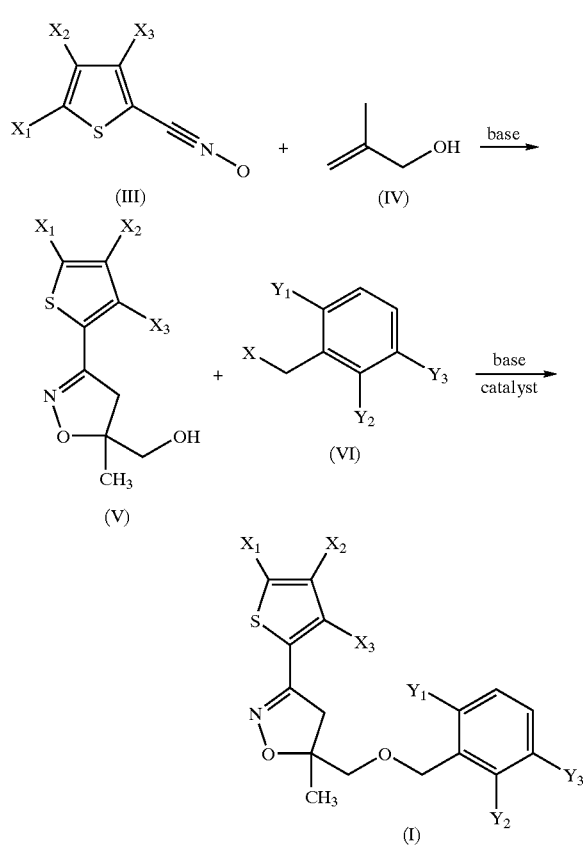

wherein,
$X_1$, $X_2$, $X_3$, $Y_1$, $Y_2$ and $Y_3$ represent each as defined above; and X represents a halogen atom, methansulfonyloxy, or toluenesulfonyloxy.

6. The process according to claim 5, wherein the base in step a) is selected from the group consisting of organic bases including triethylamine, trimethylamine and diisopropylethylamine, and inorganic bases including $K_2CO_3$, $CaCO_3$ and $Na_2CO_3$.

7. The process according to claim 5, wherein reaction is carried out in the presence of the organic solvent selected from the group consisting of $C_1$–$C_4$ alchohol, benzene, toluene, tetrahydrofuran, ethyl ether, dimethylformamide and dimethylacetamide.

8. The process according to claim 5, wherein the base in step b) is selected from the group consisting of metal hydride, metal alkoxide, metal amide or metal alkylamide and alkyl metal.

9. The process according to claim 5, wherein the base in step b) is selected from the group consisting of lithium hydride, calcium hydride, sodium alkoxide, potassium alkoxide, lithium diisopropylamide, lithium amide, lithium diisopropylamide and t-butyl lithium.

10. The process according to claim 5, wherein the catalyst in step b) is selected from the group consisting of $I_2$, NaI, KI and tetrabutylammonium iodide.

11. The herbicidal composition comprising an effective amount of the 5-benzyloxymethyl-1,2-isoxazoline derivatives according to claim 1 as an effective ingredient.

12. The herbicidal composition according to claim 11, wherein the composition is characterized in controlling paddy weeds in the paddy field rice crops comprising ECHOR (*Echinochloa crus-galli* var. *oryzicola*), SCPJU (*Scirpus juncoides* ROXB), MOOVA (*Monochoria vaginalis* PRESL), CYPSE (*Cyperus serotinus* ROTTB), and SAGPY (*Sagittaria pygmaea* MTQ).

13. The herbicidal composition according to claim 11, wherein the composition further comprises one or more additional known herbicides, insecticides, fungicides, vermicides, plant-growth regulators, fertilizers or other agricultural chemicals.

* * * * *